US011325109B2

(12) United States Patent
Wen et al.

(10) Patent No.: US 11,325,109 B2
(45) Date of Patent: May 10, 2022

(54) HETEROPOLYACID SALT CATALYSTS AND THEIR PREPARATION METHOD

(71) Applicants: Shanghai HuaYi New Material Co., Ltd., Shanghai (CN); Shanghai HuaYi Acrylic Acid Co., Ltd., Shanghai (CN)

(72) Inventors: Xin Wen, Shanghai (CN); Ge Luo, Shanghai (CN); Xinlei Jin, Shanghai (CN); Chunhua Qin, Shanghai (CN); Tonghao Wu, Shanghai (CN); Yan Zhuang, Shanghai (CN); Jianxue Ma, Shanghai (CN); Xiaodong Chu, Shanghai (CN); Jinhua Ji, Shanghai (CN)

(*) Notice: Subject to any disclaimer, the term of this patent is extended or adjusted under 35 U.S.C. 154(b) by 466 days.

(21) Appl. No.: 14/959,469

(22) Filed: Dec. 4, 2015

(65) Prior Publication Data

US 2016/0184807 A1 Jun. 30, 2016

(30) Foreign Application Priority Data

Dec. 26, 2014 (CN) .......................... 201410848273.1

(51) Int. Cl.
*B01J 37/02* (2006.01)
*B01J 27/199* (2006.01)
*C07C 51/25* (2006.01)
*B01J 37/00* (2006.01)
*B01J 35/02* (2006.01)

(52) U.S. Cl.
CPC ........... *B01J 27/199* (2013.01); *B01J 35/023* (2013.01); *B01J 37/0018* (2013.01); *B01J 37/0045* (2013.01); *C07C 51/252* (2013.01)

(58) Field of Classification Search
CPC . B01J 27/00; B01J 27/14; B01J 27/186; B01J 27/198; B01J 27/19; B01J 27/1853; B01J 27/1856; B01J 27/185; B01J 27/182; B01J 27/199; B01J 37/00; B01J 37/08; B01J 37/0045; B01J 37/04; B01J 37/0236; B01J 37/0018; B01J 37/02; B01J 35/023; C07C 57/04; C07C 51/252; C07C 51/00
See application file for complete search history.

(56) References Cited

U.S. PATENT DOCUMENTS

| 3,959,182 | A | * | 5/1976 | Izawa | B01J 23/28 502/312 |
|---|---|---|---|---|---|
| 4,075,244 | A | * | 2/1978 | Akiyama | B01J 23/002 502/209 |
| 4,489,170 | A | * | 12/1984 | Krabetz | B01J 27/19 502/211 |
| 4,558,028 | A | | 12/1985 | Tsuneki et al. | |
| 4,595,778 | A | * | 6/1986 | Duembgen | B01J 23/002 203/DIG. 21 |
| 4,966,877 | A | * | 10/1990 | Langerbeins | B01J 23/002 502/209 |
| 5,215,952 | A | * | 6/1993 | Bielmeier | B01J 23/002 502/209 |
| 6,429,332 | B1 | | 8/2002 | Tanimoto et al. | |
| 7,939,692 | B2 | * | 5/2011 | Glaser | B01J 23/44 568/357 |
| 9,314,772 | B2 | | 4/2016 | Wen et al. | |
| 2014/0141964 | A1 | * | 5/2014 | Wen | B01J 37/0009 502/178 |

FOREIGN PATENT DOCUMENTS

| CA | 1125785 A | 6/1982 |
|---|---|---|
| CN | 103831131 A | 6/2014 |

OTHER PUBLICATIONS

State Intellectual Property Office of People's Republic of China, First Office Action of corresponding Chinese Application No. 201410848273.1 with English translation, dated Dec. 4, 2017, 13 pages.
Intellectual Property of India, Examination Report, Application No. 3942/DEL/2015, dated Jun. 14, 2018, 6 pages.

* cited by examiner

*Primary Examiner* — Smita S Patel
(74) *Attorney, Agent, or Firm* — Quarles & Brady LLP

(57) ABSTRACT

Disclosed is a method for preparing a heteropolyacid salt catalyst, comprising dissolving the lead compounds for each element to prepare a suspension and dispersion slurry of catalyst precursor, which comprises all of the catalyst components; drying the catalyst precursor, mixing them with an organic compound, molding, and calcining to produce the catalyst.

2 Claims, No Drawings

HETEROPOLYACID SALT CATALYSTS AND THEIR PREPARATION METHOD

CROSS-REFERENCE TO RELATED APPLICATIONS

This Application claims priority to the Chinese Application Serial No. CN 201410848273.1, filed on Dec. 26, 2014, which is incorporated herein by reference for all purposes.

STATEMENT REGARDING FEDERALLY SPONSORED RESEARCH AND DEVELOPMENT

N/A

BACKGROUND OF THE INVENTION

Technical Field

The present invention relates to heteropolyacid salt catalysts, which can be used to oxidize (meth)acrylic aldehyde to prepare (meth) acrylic acid at high conversion rate and high selectivity under a low reaction temperature. The present invention also relates to methods for preparing the heteropolyacid salt catalysts.

Background

Gas phase oxidization of methacrolein to prepare methacrylic acid is widely used in the industry to prepare methacrylic acid. Heteropoly compounds are used as a catalyst in the method. Most heteropolyacid salt catalysts contain phosphorus and molybdenum as main components and have a structure in a form of heteropoly acid and/or salt. However, they have low reactivity, low selectivity for methacrylic acid and short working life. For these significant weaknesses, catalyst has to be replaced frequently during industrial production, resulting in increased production cost. Therefore, the prior art seeks for the improvement of the catalytic property of the heteropolyacid salt catalysts.

For example, one prior art document has disclosed a method to improve the activity of a catalyst by incorporating antimony in a special method to increase the selectivity of the catalyst. Although the catalyst prepared has improved selectivity for starting material, the method for preparing the catalyst comprises steps performed under high temperature. Thus, the reaction conditions are relatively rigorous.

Another prior art document has disclosed a method for prolonging the working life of a catalyst, comprising controlling the reaction conditions, i.e., controlling the reaction space velocity to 500~750 h$^{-1}$. Although this method could prolong the working life of the catalyst, it greatly reduces the capacity of the device, and thus influences the benefit of the device.

It has reported a method for preparing a heteropolyacid catalyst, comprising: drying an aqueous fluid containing raw materials for catalyst components to form a dried substance having an apparent density (X) of 1.00 to 1.80 kg/L; and molding the dried substance or a mixture comprising the dried substance to form a molded catalyst having a density (Y) of 1.60 to 2.40 kg/L and an X/Y ratio of 0.50 to 0.80. However, this method has complicated processes and thus the work efficiency is influenced.

It has disclosed a catalyst for preparing methacrylic acid, its preparation method comprising the following steps:

(i) mixing precursor compounds and drying by evaporation;

(ii) drying the resultant solid at about 130° C. for 16 hours;

(iii) adding therein to polymethyl methacrylate particles having a special particle size; and (iv) molding the obtained mixture under pressure, and heat treating at about 380° C. for about 5 hours in air, to produce the catalyst.

Although this method could improve the selectivity and conversion rate of the catalyst to some extent, there is still room for further improvement.

Therefore, there is a need in developing heteropolyacid salt catalysts for preparing (meth) acrylic acid, which can be used to oxidize (meth)acrylic aldehyde to prepare (meth) acrylic acid at high conversion rate and high selectivity under a low reaction temperature.

Methods for preparing the above-mentioned heteropolyacid salt catalysts are also needed in the art.

SUMMARY OF THE INVENTION

One aspect of the present invention is to provide a heteropolyacid salt catalyst for preparing (meth) acrylic acid, which can be used to oxidize (meth)acrylic aldehyde to prepare (meth) acrylic acid at high conversion rate and high selectivity under a low reaction temperature.

Another aspect of the present invention is to provide a method for preparing the heteropolyacid salt catalyst.

Therefore, in one aspect, the present invention relates to a heteropolyacid salt catalyst having the following general formula:

$$x(Mo_{12}P_aV_bD_cE_dG_eO_f)/yZ$$

wherein $Mo_{12}P_aV_bD_cE_dG_eO_f$, i.e., the heteropolyacid salt, is a main catalyst, and Z is a carrier function as a dilution heat conduction agent;

Mo, P, V and O refer to molybdenum, phosphorus, vanadium and oxygen, respectively;

D is at least one element selected from the group consisting of tungsten (W), manganese (Mn), antimony (Sb), arsenic (As) or zinc (Zn);

E is at least one element selected from the group consisting of copper (Cu), cobalt (Co), nickel (Ni), palladium (Pd), iron (Fe), cerium (Ce) or lead (Pb);

G is at least one element selected from the group consisting of potassium (K), sodium (Na), rubidium (Rb), cesium (Cs), calcium (Ca), magnesium (Mg) or barium (Ba);

Z, a dilution heat conduction agent, is selected from the group consisting of SiC, SiO$_2$, WO$_3$, TiO$_2$ and ZrO$_2$, or a mixture of two or more thereof, preferably SiC, SiO$_2$, TiO$_2$ and ZrO$_2$ or a mixture of two or more thereof;

a, b, c, d, e and f respectively refer to the atom ratio of each element, based on the mole amount of Mo being 12, and a=0.1~3, b=0.1~2, c=0.1~3, d=0.01~2, e=0.0~12, and f is the atom ratio of oxygen required for satisfying the valence of each above-mentioned component;

x and y refer to the amount of the main catalyst and the amount of the dilution heat conduction agent Z, respectively;

$$y/x=10~50\% \text{ (wt)};$$

the catalyst is prepared by the following method:

(i) dissolving precursors of the elements in the catalyst to prepare a suspension comprising all the catalyst components, obtaining a catalyst precursor;

(ii) drying the catalyst precursor, mixing same with one selected from the group consisting of polyC$_{1-4}$alkyl (meth)acrylate, polystyrene, benzoic acid, chitosan, chitin or a mixture of two or more of them, molding, and calcining to produce the catalyst;

the process of calcining is selected from the group consisting of:

(a) heating to 280-320° C. in a heating rate of 1-5° C./min in an oxygen-containing atmosphere comprising 5%~55% by volume of oxygen, holding for 40-56 hours, then replacing the atmosphere to air, heating to 360-400° C., and calcining for 10-20 hours; and (b) heating to 280-320° C. in a nitrogen atmosphere, then replacing the nitrogen atmosphere to air, heating to 360-400° C. and calcining for 10-20 hours.

In another aspect, the present invention provides a method for preparing the heteropolyacid salt catalyst comprising the following steps:

(i) dissolving precursors of the elements in the catalyst to prepare a suspension comprising all the catalyst components, obtaining a catalyst precursor;

(ii) drying the catalyst precursor, mixing the dried catalyst precursor with one selected from the group consisting of polyC$_{1-4}$alkyl (meth)acrylate, polystyrene, benzoic acid, chitosan, and chitin, or a mixture of two or more thereof, molding, and calcining to produce the catalyst;

the process of calcining is selected from the group consisting of:

(a) heating to 280-320° C. in a heating rate of 1-5° C./min in an oxygen-containing atmosphere comprising 5%~55% by volume of oxygen, holding for 40-56 hours, then replacing the atmosphere to air, heating to 360-400° C. and calcining for 10-20 hours; and (b) heating to 280-320° C. in a nitrogen atmosphere, then replacing the nitrogen atmosphere to air, heating to 360-400° C. and calcining for 10-20 hours.

SPECIFIC MODE FOR CARRYING OUT THE INVENTION

A. Catalyst and its Preparation Method

The heteropolyacid salt catalyst of the present invention has the following general formula:

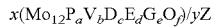

$x(Mo_{12}P_aV_bD_cE_dG_eO_f)/yZ$ which comprises a main catalyst, the heteropolyacid salt, and a carrier function as a heat conduction agent.

In the heteropolyacid salt catalyst of the present invention represented by the above general formula, Mo, P, V and O refer to molybdenum, phosphorus, vanadium and oxygen, respectively;

D is at least one element selected from the group consisting of tungsten (W), manganese (Mn), antimony (Sb), arsenic (As) or zinc (Zn); preferably at least one element selected from the group consisting of tungsten (W), antimony (Sb), or arsenic (As); more preferably antimony (Sb);

E is at least one element selected from the group consisting of copper (Cu), cobalt (Co), nickel (Ni), palladium (Pd), iron (Fe), cerium (Ce) or lead (Pb); preferably at least one element selected from the group consisting of copper (Cu), nickel (Ni), iron (Fe), cerium (Ce) or lead (Pb); and more preferably copper (Cu) and/or iron (Fe);

G is at least one element selected from the group consisting of potassium (K), sodium (Na), rubidium (Rb), cesium (Cs), calcium (Ca), magnesium (Mg) or barium (Ba); preferably at least one element selected from the group consisting of potassium (K), sodium (Na), cesium (Cs), or magnesium (Mg); and more preferably potassium (K) and/or sodium (Na);

Z, a dilution heat conduction agent, is selected from the group consisting of SiC, SiO$_2$, WO$_3$, TiO$_2$ and ZrO$_2$, or a mixture of two or more thereof; preferably SiC, SiO$_2$, TiO$_2$ and ZrO$_2$ or a mixture of two or more thereof; and more preferably SiC and/or SiO$_2$;

a, b, c, d, e and f respectively refer to the atom ratio of each element based on Mo Being 12;

a=0.1~3, preferably 0.5-2.8, more preferably 0.8-2.5, more preferably 1.2-2.0, most preferably 1.5-1.8;

b=0.1~2, preferably 0.5-1.8, more preferably 0.8-1.6, more preferably 1.0-1.5, most preferably 1.2-1.4;

c=0.1~3, preferably 0.5-2.8, more preferably 0.8-2.5, more preferably 1.2-2.0, most preferably 1.5-1.8;

d=0.01~2, preferably 0.05-1.8, more preferably 0.08-1.6, more preferably 0.1-1.4, most preferably 0.5-1.2;

e=0.01~2, preferably 0.05-1.8, more preferably 0.08-1.6, more preferably 0.1-1.4, most preferably 0.5-1.2;

f is the atom ratio of oxygen required for satisfying the valence of each above-mentioned component;

x and y refer to the amount of the main catalyst and the dilution heat conduction agent, respectively;

y/x=10~50% (wt); preferably 15-45%, more preferably 20-40%, more preferably 22-38%, and most preferably 25-35%.

DETAILED DESCRIPTION OF THE INVENTION

The method for preparing the present catalyst comprises the following steps:

1. Dissolving the precursors of the elements in the catalyst to prepare a suspension comprising all the catalyst components, obtaining a catalyst precursor;

The term "precursor of element" used herein refers to a water-soluble compound or oxide comprising an element necessary for the catalyst. For example, the precursor of molybdenum include molybdenum trioxide, ammonium paramolybdate, phosphomolybdic acid, and/or molybdate; the precursor of tungsten include tungstate and/or tungsten trioxide; the precursors of alkali metal or alkaline earth metal include hydroxide, nitrate or oxide thereof; and the precursors of other elements include acetate, nitrate, chloride or oxide, preferably ammonium salt and nitrate, thereof.

In one embodiment of the present invention, the method for preparing the suspension of the catalyst precursor comprises the following steps:

a) Preparing solution A, solution B and solution C;

b) Mixing the three solutions at 40-80° C. to prepare a suspension catalyst precursors comprising all the catalyst components.

Solution A is prepared by dissolving at least the precursors of molybdenum, phosphorus and vanadium in a solvent. In addition to the elements of molybdenum, phosphorus and vanadium, solution A may further comprise oxygen and ammonium radical.

In one embodiment of the present invention, as raw materials of catalyst for preparing solution A, molybdenum-containing compounds can be one selected from the group consisting of molybdenum trioxide, ammonium paramolybdate, phosphomolybdic acid, and molybdate, etc., preferably ammonium paramolybdate; phosphorus-containing compounds can be one selected from the group consisting of phosphorus pentoxide, phosphoric acid, phosphomolybdic acid, and ammonium phosphate, etc., preferably phosphoric acid; and vanadium-containing compounds can be one selected from the group consisting of vanadium pentoxide and ammonium metavanadate, etc., preferably ammonium metavanadate.

The solvents and temperatures for preparing solution A are not restricted, as long as the used compounds can be completely dissolved or can be uniformly mixed. Examples of solvents include, but not limit to, water, ethanol, acetone, ethyl ether, etc., preferably water.

When water is used, the amount of water is about 100-300 parts by weight, preferably 100-150 parts by weight, per 100 parts by weight of the compounds for preparing the slurry.

Solution B can be prepared by dissolving at least a compound containing G and a compound containing D in a solvent. The compound containing G and the compound containing D may be the nitrate, acetate, chloride or oxide of the G element and the D element.

The solvents and temperatures for preparing solution B are not restricted, as long as the used compounds can be completely dissolved or can be uniformly mixed. Examples of solvents include, but not limit to, water, ethanol, acetone, ethyl ether, etc., preferably water. In one embodiment of the present invention, the solvent used for preparing solution B is identical to the solvent used for preparing solution A.

When water is used, the amount of water is about 200-800 parts by weight, preferably 300-400 parts by weight, per 100 parts by weight of the compounds for preparing the slurry.

Solution C can be prepared by dissolving at least a compound containing E in a solvent. The compound containing E may be the nitrate, acetate, chloride or oxide of the E element.

The solvents and temperatures for preparing solution C are not restricted, as long as the used compounds can be completely dissolved or can be uniformly mixed. Examples of solvents include, but not limit to, water, ethanol, acetone, ethyl ether, etc., preferably water.

When water is used, the amount of water is about 100-800 parts by weight, preferably 200-300 parts by weight, per 100 parts by weight of the compounds for preparing the slurry.

The process for mixing solutions A, B and C together are not restricted, it can be any method known in the art. For example, solutions A, B and C can be mixed together in arbitrary order. For example, solution A may be mixed firstly with solution B to produce a mixture of A and B, and then the mixture of A and B is mixed with solution C; solution A may be mixed firstly with solution C to produce a mixture of A and C, and then the mixture of A and C is mixed with solution B; solution B may be mixed firstly with solution C to produce a mixture of B and C, and then the mixture of B and C is mixed with solution A. Preferably, solution A is mixed firstly with solution B to produce a mixture of A and B, and then the mixture of A and B is mixed with solution C. Generally, mixing is performed while stirring to produce homogenous suspension.

The temperature under which solutions A, B and C are mixing is not restricted and can be any temperature known in the art. In one embodiment of the present invention, mixing is performed under 40-80° C., preferably 40-60° C. More preferably, the three solutions are mixed under 50-60° C.

2. Drying and Molding the Dried Catalyst Precursors and Organic Compounds

The process and temperature for drying the suspension are not specifically limited and can be any ones known in the art, for example, drying by spray, by evaporation, by drum, etc, with spray drying preferred.

If desired, the dried catalyst precursor can be ground. The grinding process is not specifically limited and can be any conventional one in the art. For example, ball milling can be used to grind the dried catalyst precursor.

The present method further comprises steps of mixing the dried and optionally ground catalyst precursor, the dilution heat conduction agent, and the organic compound together and molding same. The organic compound used in the present invention may be added at any time during preparation. For example, the organic compound of the present invention is added during mixing the dried catalyst precursor and the dilution heat conduction agent.

In one embodiment of the present invention, examples of the organic compound include, but not limit to, poly$C_{1-4}$alkyl (meth)acrylate, such as polymethyl acrylate, polymethyl methacrylate, polyethyl acrylate, polyethyl methacrylate, polypropyl acrylate, polypropyl methacrylate, poly(n-butyl acrylate), poly(n-butyl methacrylate), poly(t-butyl acrylate), poly(t-butyl methacrylate); polystyrene; benzoic acid, chitosan or chitin, or mixtures of two or more thereof.

In one embodiment of the present invention, the organic compound is a polymer having a weight average molecular weight of 5000-80000, preferably 7,000-50,000, more preferably 8,000-10,000. As mentioned above, the polymer may be selected from the group consisting of poly$C_{1-4}$alkyl (meth)acrylate, polystyrene, or mixture thereof.

In a preferred embodiment of the present invention, benzoic acid is used as the organic compound.

The addition amount of the organic compound, based on the molar amount of the molybdenum element in the catalyst, is 0.03-0.3 (the ratio of the organic compound/Mo=0.03-0.3, molar ratio), preferably 0.05-0.25, more preferably 0.08-0.22, more preferably 0.10-0.20, most preferably 0.12-0.18.

The organic compound of the present invention can be added in any time during preparing the catalyst precursor, preferably during molding and added together with the dilution heat conduction agent. Suitable dilution heat conduction agent is SiC, $MoO_3$, $WO_3$, $TiO_2$ or $ZrO_2$ or a mixture of two or more thereof, preferably SiC, $MoO_3$, $ZrO_2$ or a mixture of two or more thereof.

If x and y refer to the amounts of the prepared main catalyst ($Mo_{12}P_aV_bD_cE_dG_eO_f$) and the dilution heat conduction agent (Z), respectively, the weight ratio of y and x (y/x) is 11.1-50%, preferably 15-45%, more preferably 20-40%, even more preferably 22-38%, and most preferably 25-35%.

The process for molding the catalyst is not specifically limited. Any known dry molding or wet molding method can be used, such as pelleting, extrusion, and granulation, etc. The shape of the formed green body is not specifically limited, which may be any required shape such as cylindrical, circular, spherical, etc. Additionally, a little amount of lubricant, such as graphite, may be added when molding.

3. Calcination

The present method further comprises a step of calcining the molded catalyst to produce a finished product.

The inventors of the present application find that the calcining is closely associated with the selectivity and catalytic efficiency of the final catalyst. If a special calcining method is used, the performance of the catalyst can be advantageously improved.

Therefore, the calcining process of the present invention comprises:

(a) Heating to 280-320° C. in a heating rate of 1-5° C./min in an oxygen-containing atmosphere comprising 5%~55% by volume of oxygen, preferably 10%~50% by volume of oxygen, more preferably 15%~45% by volume of oxygen, and even more preferably 25%~40% by volume of oxygen, holding for 40-56 hours, then replacing the atmosphere to air, heating to 360-400° C. and calcining for 10-20 hours.

The inventors finds that, when calcining is performed in an oxygen-containing atmosphere, the performance of the catalyst can be advantageously improved by slowly heating, holding at predetermined temperature for a predetermined period, and then heating at an elevated temperature.

In the process of the present invention, the heating rate in the oxygen-containing atmosphere is 1-5° C./min, preferably 2-4° C./min, and more preferably about 3° C./min. When heating to 280-320° C., preferably 290-310° C., and more preferably about 300° C., the calcined material is held for 40-56 hours, preferably 42-54 hours, more preferably 44-50 hours, and most preferably 46-48 hours. The atmosphere is then replaced by air and the temperature is raised to 360-400° C., preferably 365-395° C., more preferably 370-390° C., and most preferably 375-385° C., and the material is calcined at this temperature for 10-20 hours, preferably 12-18 hours, and more preferably 14-16 hours.

Alternatively, the calcining process may comprise:

(b) heating to 280-320° C. in a nitrogen atmosphere, then replacing the nitrogen atmosphere to air, heating to 360-400° C. and calcining for 10-20 hours.

In this process, the calcination can be divided into two stages, one is performed in a nitrogen atmosphere, the temperature thereof can be raised to 280-320° C., preferably 290-310° C., more preferably about 300° C., by a conventional heating rate. In one embodiment, the heating rate is 10-25° C./min, and preferably 15-20° C./min. After reaching the above predetermined temperature, the atmosphere is changed into air, and then the temperature is further raised to 360-400° C., preferably to 365-395° C., more to preferably 370-390° C., and most to preferably 375-385° C. Calcination is carried out at this temperature for 10-20 hours, preferably 12-18 hours, more preferably 14-16 hours.

The oxygen-containing atmosphere used during the calcination may be derived from air or may be a diluted atmosphere containing $O_2$. The molecular oxygen may be from pure oxygen, and oxygen-rich gas or air, and the gas for dilution may be $N_2$, He or Ar, or mixture thereof in any ratio. The content of oxygen is 5~55% by volume.

In one embodiment of the present invention, the main catalyst may be selected from the group consisting of $Mo_{12}P_{1.4-1.6}K_{1.1-1.3}V_{0.4-0.6}Sb_{0.4-0.6}Cu_{0.1-0.3}$ (such as $Mo_{12}P_{1.5}K_{1.2}V_{0.5}Sb_{0.5}Cu_{0.2}$, $Mo_{12}P_{1.45}K_{1.15}V_{0.55}Sb_{0.55}Cu_{0.2}$ and $Mo_{12}P_{1.55}K_{1.2}V_{0.5}Sb_{0.5}Cu_{0.2}$, $Mo_{12}P_{1.5}K_{1.25}V_{0.5}Sb_{0.6}Cu_{0.2}$) and $Mo_{12}P_{1.4-1.5}K_{1.1-1.3}V_{0.4-0.6}Sb_{0.4-0.6}Fe_{0.2-0.3}$ (such as, $Mo_{12}P_{1.5}K_{1.2}V_{0.5}Sb_{0.5}Fe_{0.25}$, $Mo_{12}P_{1.45}K_{1.25}V_{0.5}Sb_{0.5}Fe_{0.25}$, $Mo_{12}P_{1.5}K_{1.2}V_{0.6}Sb_{0.6}Fe_{0.28}$).

B. Use of the Catalyst

The catalyst prepared by the above method can be used for gas phase oxidation of (meth)acrylic aldehyde to synthesize (meth)acrylic acid. In one embodiment of the present invention, the gas oxidation method comprises the following steps:

Pre-heating a mixture of methacrolein, air or a diluted molecular oxygen-containing gas and water vapor;

Loading the catalyst in a tubular fixed-bed reactor; and

Passing the pre-heated mixture to the tubular fixed-bed reactor to perform a selective oxidation to synthesize methacrylic acid.

In the diluted gas mixture containing molecular oxygen used in the present invention, the molecular oxygen may be derived from pure oxygen, an oxygen rich gas or air, and the gas for dilution may be $N_2$, CO, $CO_2$ or $H_2O$ or mixture thereof in any ratio.

The reaction conditions of the present method include a temperature of 220-300° C., preferably 240-280° C.; a pressure of 0.05-0.5 MPa, preferably atmospheric pressure; a total space velocity of 1000~5000 $h^{-1}$, preferably 1200~3000 $h^{-1}$ for the gas mixture; a molar concentration of 1~20%, preferably 3~20%, for MAL; a molar ratio between $O_2$ and methacrolein of 0.5~8 preferably 1~5; and a molar ratio of between water vapor and methacrolein of 1~15, preferably 3~10.

The conversion rate, selectivity and yield of methacrylic acid oxidized from methacrolein can be calculated according to the following equations:

Conversion Rate (mol %)=(mole of reacted methacrolein)/(mole of supplied methacrolein)×100

Selectivity (mol %)=(mole of produced methacrylic acid)/(mole of reacted methacrolein)×100

Yield (mol %)=(mole of produced methacrylic acid)/(mole of supplied methacrolein)×100.

The method for preparing the present catalyst and the reaction performance of the catalyst in catalyzing methacrolein to selectively oxidize it to produce methacrylic acid will be further illustrated by the following examples. The scope of the present invention shall not be limited to these examples. For example, it is well known in the art that the catalyst of the present invention can be used to catalyze acrolein to selectively oxidize it to produce acrylic acid.

Example 1

1. Preparation of Catalyst (a) Preparation of Catalyst Precursor 400 g ammonium paramolybdate, 11.1 g ammonium metavanadate and 32.3 g phosphoric acid were dissolved in 800 g distilled water to produce solution A. 22.8 g potassium nitrate and 13.7 g antimony oxide were mixed in 100 g distilled water to produce suspension B. And 9.2 g copper nitrate was dissolved in 20 g distilled water to produce solution C.

Solution A was heated to 60° C. and suspension B was added into solution A with stirring over a period of 10 minutes. After stirring for 10 minutes, solution C was added to the mixture of A and B to produce a mixture of A, B and C. The mixture was stirred under 60° C. for 2 hours to produce a slurry containing catalyst precursor.

The slurry was dried by spray to produce 440 g solid powder. 22.5 g benzoic acid, 77.6 g SiC, 11 g graphite and suitable amount of distilled water were added to the solid powder. The thus obtained mixture was extruded and prepared into particles having a particle size of about 15 mesh.

(b) Calcination

The particles obtained above were placed in air and heated to 280° C. in a heating rate of 4° C./min and then held for 40 hours. After that, the temperature was raised to 360° C. and the particles were calcined for 15 hours to produce the finished catalyst. The composition of the catalyst was $85(Mo_{12}P_{1.5}K_{1.2}V_{0.5}Sb_{0.5}Cu_{0.2})/15$ SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Example 2

1. Preparation of Catalyst

Catalyst was prepared according to Example 1, except that the 22.5 g benzoic acid used in Example 1 was changed to 55 g benzoic acid.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Comparative Example 1

1. Preparation of Catalyst

The steps of Example 1 were repeated, except that the following calcining method was carried out:

The particles obtained were placed in air and heated to 360° C. in a heating rate of 15° C./min and then calcined for 15 hours to produce the finished catalyst having a composition of 85(Mo$_{12}$P$_{1.5}$K$_{1.2}$V$_{0.5}$Sb$_{0.5}$Cu$_{0.2}$)/15 SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Comparative Example 2

1. Preparation of Catalyst

The steps of Example 1 were repeated, except that the following calcining method was carried out:

The particles obtained were placed in air and heated to 280° C. in a heating rate of 4° C./min, and, after then, the temperature was directly raised to 360° C. and then calcined for 15 hours to produce the finished catalyst. The composition of the catalyst is 85(Mo$_{12}$P$_{1.5}$K$_{1.2}$V$_{0.5}$Sb$_{0.5}$Cu$_{0.2}$)/15 SiC. The reaction results were shown in Table 1.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmosphere pressure, 265° C., and a space velocity of 1100 h$^{-1}$. The reaction results were shown in Table 1.

Example 3

1. Preparation of Catalyst (1) Preparation of Catalyst Precursor 400 g ammonium paramolybdate, 11.1 g ammonium metavanadate and 32.3 g phosphoric acid were dissolved in 800 g distilled water to produce solution A. 22.8 g potassium nitrate, 22.5 g benzoic acid and 13.7 g antimony oxide were mixed in 100 g distilled water to produce suspension B. And 9.2 g copper nitrate was dissolved in 20 g distilled water to produce solution C.

Solution A was heated to 60° C. and suspension B was added into solution A with stirring over a period of 10 minutes. After stirring 10 minutes, solution C was added to the mixture of A and B to produce a mixed slurry of A, B and C. The mixed slurry was stirred under 60° C. for 2 hours to produce a slurry containing the catalyst precursor.

The slurry was dried by spray. 77.6 g SiC, 11 g graphite and suitable amount of distilled water were added. The thus obtained mixture was extruded and prepared into particles having a particle size of about 15 mesh.

(b) Calcination

The particles obtained above were placed in nitrogen atmosphere and heated to 290° C. in a heating rate of 15° C./min and then air was introduced and the temperature was further raised to 360° C. and held for 15 hours to produce the finished catalyst. The composition of the catalyst was 85(Mo$_{12}$P$_{1.5}$K$_{1.2}$V$_{0.5}$Sb$_{0.5}$Cu$_{0.2}$)/15 SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Example 4

1. Preparation of Catalyst

Catalyst was prepared according to Example 3, except that the 22.5 g benzoic acid used in Example 3 was changed to 48 g chitosan.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Example 5

1. Preparation of Catalyst

Catalyst was prepared according to Example 3, except that the 22.5 g benzoic acid used in Example 3 was changed to 11 g benzoic acid.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

Example 6

1. Preparation of Catalyst

Catalyst was prepared according to Example 3, except that the 9.2 g copper nitrate used in Example 3 was changed to 19.3 g ferric nitrate. The composition of the catalyst was 85($Mo_{12}P_{1.5}K_{1.2}V_{0.5}Sb_{0.5}Fe_{0.25}$)/15 SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure, 265° C., and a space velocity of 1100 h$^{-1}$. The reaction results were shown in Table 1.

TABLE 1

|  | Reaction Temerature/ ° C. | MAL conversion rate/% | MAA selectivity/ % | MAA yield/ % |
| --- | --- | --- | --- | --- |
| Example 1 | 265 | 78.4 | 85.2 | 66.8 |
| Example 2 | 265 | 79.9 | 86.5 | 69.1 |
| Comparative Example 1 | 265 | 47.2 | 72.1 | 34.0 |
| Comparative Example 2 | 265 | 53.4 | 75.6 | 40.4 |
| Example 3 | 265 | 79.9 | 83.1 | 66.4 |
| Example 4 | 265 | 78.8 | 84.0 | 66.2 |
| Example 5 | 265 | 79.1 | 84.9 | 67.2 |
| Example 6 | 265 | 78.9 | 82.2 | 64.9 |
| Example 7 | 265 | 80.5 | 80.1 | 64.5 |

The above results show that the catalytic performance could be advantageously improved when a special calcination process is used.

Comparative Example 3

1. Preparation of Catalyst (1) Preparation of Catalyst Precursor
400 g ammonium paramolybdate, 11.1 g ammonium metavanadate and 32.3 g phosphoric acid were dissolved in 800 g distilled water to produce solution A. 22.8 g potassium nitrate and 13.7 g antimony oxide were mixed in 100 g distilled water to produce suspension B. And 9.2 g copper nitrate was dissolved in 20 g distilled water to produce solution C.

Solution A was heated to 60° C. and suspension B was added into solution A with stirring over a period of 10 minutes. After stirring 10 minutes, solution C was added to the mixture of A and B to produce a mixed slurry of A, B and C. The mixed slurry was stirred under 60° C. for 2 hours to produce a slurry containing the catalyst precursor.

The slurry was dried by spray to produce 440 g solid powder. 77.6 g SiC, 11 g graphite and suitable amount of distilled water were added to the solid powder. The thus obtained mixture was extruded and prepared into particles having a particle size of about 15 mesh.

(b) Calcination
The particles obtained above were placed in air and heated to 280° C. in a heating rate of 4° C./min and then held for 40 hours. After that, the temperature was raised to 360° C. and the particles were calcined for 15 hours to produce the finished catalyst. The composition of the catalyst is 85($Mo_{12}P_{1.5}K_{1.2}V_{0.5}Sb_{0.5}Cu_{0.2}$)/15 SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure and a space velocity of 1100 h$^{-1}$. The reaction results were shown in Table 2.

Comparative Example 4

1. Preparation of Catalyst (1) Preparation of Catalyst Precursor
400 g ammonium paramolybdate, 11.1 g ammonium metavanadate and 32.3 g phosphoric acid were dissolved in 800 g distilled water to produce solution A. 22.8 g potassium nitrate and 13.7 g antimony oxide were mixed in 100 g distilled water to produce suspension B. And 9.2 g copper nitrate was dissolved in 20 g distilled water to produce solution C.

Solution A was heated to 60° C. and suspension B was added into solution A with stirring over a period of 10 minutes. After stirring 10 minutes, solution C was added to the mixture of A and B to produce a mixed slurry of A, B and C. The mixed slurry was stirred under 60° C. for 2 hours to produce a slurry containing the catalyst precursor.

The slurry was dried by spray to produce 440 g solid powder. 77.6 g SiC, 11 g graphite and suitable amount of distilled water were added to the solid powder. The thus obtained mixture was extruded and prepared into particles having a particle size of about 15 mesh.

(b) Calcination
The particles obtained were placed in air and heated to 280° C. in a heating rate of 15° C./min, then the temperature was directly raised to 360° C. and the particles were calcined for 15 hours to produce the finished catalyst. The composition of the catalyst is 85($Mo_{12}P_{1.5}K_{1.2}V_{0.5}Sb_{0.5}Cu_{0.2}$)/15 SiC.

2. Catalytic Oxidation

The catalyst was filled into a reaction tube. A mixed gas consisting of 5% by volume of methacrolein, 10% by volume of oxygen, 40% by volume of nitrogen, and 45% by volume of water vapor was introduced. Reaction was carried out under atmospheric pressure and a space velocity of 1100 h$^{-1}$. The reaction results were shown in Table 2.

TABLE 2

|  | Reaction Temperature/ ° C. | MAL conversion rate/% | MAA selectivity/ % | MAA yield/ % |
| --- | --- | --- | --- | --- |
| Comparative Example 3 | 285 | 78.5 | 81.1 | 64.4 |
| Comparative Example 4 | 285 | 78.3 | 81.3 | 64.4 |

The results in Table 2 show that the performance of the finished catalyst is not substantively affected by adding or not adding the organic compound, or heating in a slow and step-wise manner.

What is claimed is:

1. A method for preparing a heteropolyacid salt catalyst, comprising the following steps:
   (i) dissolving precursors for Mo, P, V, D, E, G, and O elements in the heteropolyacid salt catalyst to prepare a suspension comprising all the heteropolyacid salt catalyst components;
   (ii) drying the suspension, mixing the dried materials with benzoic acid, molding, and calcining to produce the heteropolyacid salt catalyst;
   wherein the calcining consists of heating to 280-320° C. in a heating rate of 1-5° C./min in an oxygen-containing atmosphere comprising 5%~55% by volume of oxygen, holding for 40-56 hours, then replacing the oxygen-containing atmosphere to air, heating to 360-400° C. and calcining for 10-20 hours;
   wherein the heteropolyacid salt catalyst having the following general formula:

$$x(Mo_{12}P_aV_bD_cE_dG_eO_f)/yZ$$

wherein $Mo_{12}P_aV_bD_cE_dG_eO_f$ is a main catalyst of the heteropolyacid salt catalyst, and Z is a carrier function as a heat conduction agent;

Mo, P, V and O represent elements of molybdenum, phosphorus, vanadium and oxygen, respectively;
   D is at least one element selected from the group consisting of tungsten, manganese, antimony, arsenic and zinc;
   E is at least one element selected from the group consisting of copper, cobalt, nickel, palladium, iron, cerium and lead;
   G is at least one element selected from the group consisting of potassium, sodium, rubidium, cesium, calcium, magnesium and barium;
   Z is selected from the group consisting of SiC, $SiO_2$, $WO_3$, $TiO_2$ and $ZrO_2$, and a mixture of two or more thereof;
   a, b, c, d, e and f respectively refer to an atom ratio of each element based on a molar amount of Mo being 12, and a=0.1~3, b=0.1~2, c=0.1~3, d=0.01~2, e=0.01~2, and f is an atom ratio of oxygen required for satisfying the valence of each of the P, V, D, E, G, and O component;
   x and y refer to the amount of the main catalyst of the heteropolyacid salt catalyst and the heat conduction agent Z, respectively;
   y/x=10~50 wt. %.

2. The method according to claim 1, wherein an addition amount of benzoic acid, based on the molar amount of the molybdenum element in the heteropolyacid salt catalyst, is 0.03-0.3.

* * * * *